United States Patent [19]

DeMarco

[11] 4,141,358

[45] Feb. 27, 1979

[54] ANKLE TAPE PACK

[76] Inventor: Alexander H. DeMarco, 85 Maple Ave., Shelton, Conn. 06484

[21] Appl. No.: 816,594

[22] Filed: Jul. 18, 1977

[51] Int. Cl.² .................................................. A61F 13/06
[52] U.S. Cl. ........................................................ 128/166
[58] Field of Search ................... 128/166, 166.5, 80 D, 128/80 H, 80 R, 153, 581, 83.5, 157, 149

[56] References Cited

U.S. PATENT DOCUMENTS

| | | | |
|---|---|---|---|
| 1,544,641 | 7/1925 | Guinzburg | 128/166 |
| 1,624,266 | 4/1927 | Rider | 128/166 |
| 3,073,305 | 1/1963 | Biggs et al. | 128/166 |
| 3,312,219 | 4/1967 | Peckland | 128/166 |
| 3,357,425 | 12/1967 | Morgan | 128/166 |
| 3,508,544 | 4/1970 | Moore et al. | 128/149 |
| 3,674,023 | 7/1972 | Mann | 128/166 |
| 4,076,022 | 2/1978 | Walker | 128/153 |

Primary Examiner—Lawrence W. Trapp
Attorney, Agent, or Firm—Walter Spruegel

[57] ABSTRACT

An ankle tape pack having a strap part for form-fitting wrap on the ankle and adjoining part of a foot, and tape parts attached to the strap part for winding on the foot over the applied strap part, with the strap part being formed of two plies of which an inner ply is of sock material, and the outer ply is sufficiently stiff to resist folding on itself and is of a friction material to which the wound-on tape parts cling rather tenaciously.

3 Claims, 5 Drawing Figures

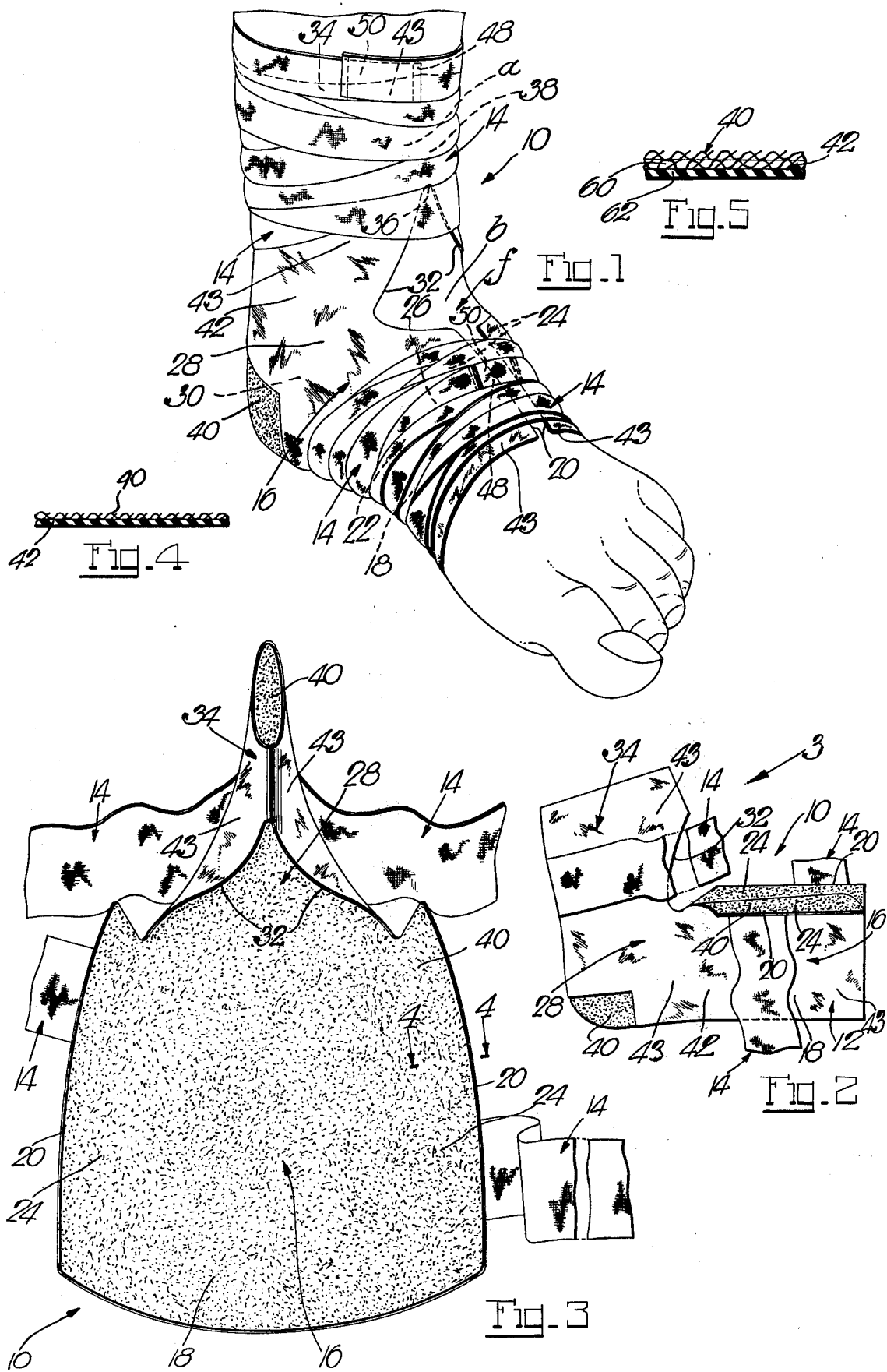

ANKLE TAPE PACK

This invention relates to ankle tapes in general, and to ankle tape packs in particular.

Ankle taping is being resorted to quite widely, though not exclusively, among those engaged in athletic activities in the course of which their ankles are subjected to rather severe and often abnormal stresses that might readily prove to be harmful to the ankles if they were not protected by taping. Taping of ankles in widely accustomed fashion, i.e., by winding a plain tape directly onto an ankle, is mostly objectionable, however, because if such a tape is wound sufficiently tightly to be held in place and not slip while in use, it will be so tight as most likely to feel quite uncomfortable and also interfere with proper blood circulation, and if the tape is wound less tightly, it will most likely unwind or slip while in use. In attempting to avoid this deficiency of plain tapes, recourse was had to various tapeless ankle straps which, however lacked any effective regulation of their form-fit with ankles to be both, comportable as well as truly protective. With such tapeless ankle straps being also deficient in their ankle-protecting function, recourse was further had to combined ankle straps and tapes which, however, proved to be also largely ineffective in their ankle-protecting function. Thus, the strap parts of these combined straps and tapes proved to be as little protective as tapeless ankle straps and served primarily for attachment of the tape parts and their orientation thereon in a manner which will be conducive to wrapping the tape parts about the applied strap parts on ankles in a planned smooth fashion that promises best protection for the ankles. Further, the tape parts of these combined ankle straps and tapes are as objectionable as plain tapes, in that the tape parts require undue tightening in order to be held in place while in use, with ensuing discomfort to the wearer, including interference with proper blood circulation, or they will unwind all too readily if wound less tightly. This is due to the fact that the tape parts, which are wound on ankles through intermediation of their associated strap parts, are held against unwinding with no greater holding force than that with which plain tapes are held on ankles on which they are wound directly.

It is a primary object of the present invention to provide an ankle tape pack in the form of a combined ankle strap and tape, of which the applied strap part serves to lock the tape part to the ankle against unwinding during most any physical activity on mere wind of the tape part to the applied strap part with a tightness at which the wearer will experience neither discomfort nor interference with proper blood circulation. With the strap part thus functioning as a secure lock against unwinding of the applied tape part, the present combined ankle strap and tape affords for the first time protective taping of an ankle without any discomfort to the wearer or danger of unwinding of the tape part during most any physical activity of the wearer.

It is another object of the present invention to provide an ankle tape pack of this type, of which the strap part functions as a lock against unwinding of the applied tape part, as aforementioned, by forming the strap part, on the one hand sufficiently pliable for its ready form-fit with an ankle, and on the other hand sufficiently stiff for its hold, when taped to an ankle, against displacement or slippage on the ankle during most any physical activity involvement of the ankle, and by further forming the strap part as a non-skid backing for the tape part to which the latter will, on its wind-on, cling with far greater tenacity than a plain tape will cling to a naked ankle. Thus, the characteristic twin features of relative stiffness and non-skid backing of the strap part, while separately making for non-skid adherence of the strap part to an ankle and for non-skid adherence of the tape part to the strap part, together make for non-slip taping of an ankle.

It is a further object of the present invention to provide an ankle tape pack of this type which, besides affording non-slip taping of an ankle by virtue of the aforementioned characteristics of relative stiffness and non-skid backing of the strap part, further affords wear of the applied strap and tape with the accustomed feel and comfort of a ordinary sock which makes it particularly persuasive and even attractive to submit or resort to protective ankle taping.

Another object of the present invention is to provide an ankle tape pack of this type which affords non-slip taping of an ankle as well as wear of the strap and tape parts with the accustomed feel and comfort of a sock, as aforementioned, by arranging the strap part in the general shape of a partial sock which fits over an ankle and the adjoining instep of a foot, and has inner and outer plies, of which the inner ply is of any desired sock fabric adapted to bear directly against the foot for its comfortable feel as a sock, and the outer ply is bonded throughout to the inner ply, with this outer ply being of a suitable pliable material of the necessary stiffness to withstand slippage on the wearer's foot during physical activity, and being also of the necessary friction to provide a non-skid backing for the tape part on its wind-on application to the applied strap part. To this end, the inner ply is preferably and conveniently a partial sock, and the outer ply may conveniently be formed on the inner sock ply by an outer coating thereon of a suitable friction material such as cured rubber, for example, which can readily be kept at a desired pliancy and affords an entirely satisfactory non-skid backing for the tape part.

Further objects and advantages will appear to those skilled in the art from the following, considered in conjunction with the accompanying drawings.

In the accompanying drawings, in which certain modes of carrying out the present invention are shown for illustrative purposes:

FIG. 1 is a fragmentary perspective view of a foot showing the applied strap and tape of an ankle tape pack which embodies the invention;

FIG. 2 is a side view of the same tape pack;

FIG. 3 is an enlarged perspective view of the featured tape pack as seen in the direction of the arrow 3 in FIG. 2;

FIG. 4 is a fragmentary section taken on the line 4—4 of FIG. 3; and

FIG. 5 is a fragmentary section through a tape pack embodying the invention in a modified manner.

Referring to the drawings, the reference numeral 10 designates an ankle tape pack which has as its principal components a strap part 12 and tape parts 14.

The strap part 12 is normally folded, and is of a shape which in its folded condition resembles, or at least suggests, a sock with its toe end cut off (FIG. 2), but which in non-folded condition bears little resemblance to a sock (FIG. 3), though it does by its shape and size lend itself to application to a foot in fair form-fit therewith (FIG. 1). To the latter end, the strap part 12 has a foot flap or section 16 of which a forward portion 18 with opposite side edges 20 may be spread out for stepping with the instep 22 of a foot f on a middle part thereof, and for folding or wrapping the opposite side wings 24 against the raised portion 26 of the instep 22 in substantial form-fit with the foot thereat at which the side edges 20 of the foot flap 16 are fairly closely spaced from each other (FIG. 1). The foot flap 16 of the strap part 12 further provides, next to the forward portion 18 thereof a rearwardly continuing portion 28 which is tailored for fairly fitting wrap around the heel 30 of the foot f when the forward portion 18 of the strap part is applied to this foot in the manner just explained, with the rear or heel portion 28 of the foot flap 16 having opposite side edges 32 which are tailored to leave a substantial part of the foot's bend b exposed (FIG. 1) so that the applied heel portion 28 of the foot flap 16 may not interfere with free bending motion of the ankle a on the foot f.

Finally, the strap part 12 has, besides the foot flap 16, an ankle portion 34 which extends upwardly from, and is continuous with, the rear heel portion 28 of the foot flap 16. Except for some extension of the opposite side edges 32 of the heel portion 28 of the foot flap 16 into, and their merger at 36 in, the ankle portion 34, the latter is over the remainder 38 of its length closed like a sock so that in applying the strap part 12 to the foot, its closed ankle portion 38 is slipped over the foot and onto the ankle, whereupon the foot flap 16 is with its forward and rear portions 18 and 28 wrapped around the instep and heel parts of the foot in fair form-fit therewith in which they are held by the subsequently applied tape parts 14 in a manner described hereinafter.

The strap part 12 is formed of two plies, namely an inner ply 40 and an outer ply 42, of which the inner ply 40 is of any suitable, preferably knit, fabric of comfortable wear. Accustomed comfortable feel and wear of the strap part 12 on the wearer's foot is thus one of the characteristics of the ankle tape pack.

The outer ply 42 is characterized by certain stiffness and friction. Thus, the outer ply 42 is of a suitable material of sufficient stiffness at which it will not fold on itself and will readily stay in form-fit with a foot against which it is held with a minimal force that really need be only a small fraction of the force with which the tape parts will, on their later described wind-on application on top of the strap part, hold the latter in form-fit with the foot. With this stiffness, the applied strap part, even though mostly wrapped only partly, rather than being completely closed, around a foot, is by the subsequently wound-on tape parts kept nevertheless in as secure and accurate form-fit with the foot as would a completely closed and painstakingly fitted strap. Even more important, the partial wrap application of the strap part 12 is particularly advantageous in that a strap part of a single given size lends itself to secure and accurate form-fit with feet of fairly widely different sizes. The other characteristic of the outer ply 42 is its friction which leaves the ply with a non-skid backing 43 on which the tape parts will be wound and to which they will cling with far greater tenacity than a plain tape will cling to a naked foot.

The inner ply 40 is, for desired comfortable wear of the strap part 12 on a wearer's foot, preferably and conveniently a partial sock, and the outer ply is bonded throughout to the inner ply, with this outer ply 42 being of a suitable pliable material of the necessary stiffness to withstand slippage on the wearer's foot during physical activity, and being also of the necessary friction to provide a non-skid backing for the tape parts 14 on their wind-on application to the applied strap part 12. The outer ply 42 may conveniently be formed on the inner sock ply 40 by an outer coating thereon of a suitable friction material, such as cured rubber or like material, for example, which can be kept rather thin for light weight and desired stiffness, and affords an entirely satisfactory non-skid backing for the tape parts. The outer ply 42 may be provided on the inner sock ply 40 by applying thereto a coating of latex, for example, and permitting it to set by exposure to the atmosphere or applying an accelerator thereto, or a fairly thin sheet of uncured rubber may be applied, by roll-on, for example, to the inner ply 40 and then cured by the application of heat and pressure.

The tape parts 14, of which two are provided on the foot flap 16, and two more are in this instance provided on the ankle portion 38, of the strap part 12, are preferably of the usual, closely woven, tape material which has a texture that clings rather well to, and does not readily slip on, a tape winding underneath, wherefore these tape parts 14 cling with particular tenacity to the non-skid backing afforded by the outer ply of the applied strap part. The tape parts 14 may be suitably attached to the outer ply 42 of the strap part 12. The tape parts 14 have free lengths which together preferably approximate the full length of a plain tape customarily used for directly taping an ankle, thereby to have available sufficient tape length for truly protective taping of an ankle. Also, the tape parts 14 are, in their attachement to the strap part 12, oriented and coordinated for their winding application in a manner for best protective tapling results. Some or all of the tape parts 14 are preferably provided with suitable detachable securing means such as Velcro, each of which comprises in combination a fabric pad 48 and a fabric portion 50 of a plurality of mono-filament hooks which when pressed against the fabric pad 48 will engage the same and hold the parts together.

In applying the tape pack to a foot, the strap part 12 is with the closed end of the ankle portion 38 slipped over the foot and onto the ankle, whereupon the foot flap 16 is wrapped against the instep and heel of the foot. The tape parts 14 are next wound onto the applied strap part 12 preferably in a predetermined sequence and in a manner suggested to some extent by the orientation of their attachment to the foot flap, and well distributed over the expanse of the strap part (FIG. 1), with the wound tape parts being, besides their considerable hold on the non-skid backing on the strap part, further held in position at their ends by closing the Velcro-type securing means 48,50.

The present ankle tape pack secures a number of advantages. Thus, it is in its wear of the accustomed feel and comfort of a sock owing to the featured sock make-up of the inner ply 40 of the strap part 12. Further, the hold of the wound-on tape parts 14 on a foot through intermediation of the applied strap part is particularly secure and does not allow slippage of the tape parts in the course of most any physical acticity, owing to the featured stiffness of the strap part which prevents creep or displacement of any portion thereof on the foot, coupled with the further featured non-skid backing afforded by the outer ply 42 to which the wound tape parts cling quite tenaceously. Also, since the wound-on tape parts are held particularly secure against unwinding or loosening, it stands to reason that these tape parts can readily be wound with no more than reasonable tightness at which they will securely be held in place during most any physical activity, yet will cause no discomfort to the wearer for the longest time.

While in the foregoing description the use of sock material for the inner ply 40 was mentioned, the inner ply may also be of another material, such as a woven fabric, for example, to which a coating of cured rubber or the like may readily be applied. It has also been found that such other material may advantageously be stretchable for particularly smooth and ready form-fit of the outer ply with a wearer's foot. Finally, it is entirely feasible to provide the outer ply in the form of a stretch fabric 60 (FIG. 5) with an outer coating 62 of cured rubber or the like, and secure this outer ply to an inner ply 40 of suitable sock material, for example, by coating the interfaces thereof with a suitable rubber-like adhesive such as latex, for example, and pressing them together.

What is claimed is:

1. An ankle tape pack, comprising a strap having inner and outer plies and being shaped for wear on an ankle and adjoining instep of a foot, and tapes attached with one end to said strap and adapted for winding on said strap when worn on an ankle and adjoining instep of a foot to thereby hold the ankle taped, with said inner ply being of sock material for direct wear on a wearer's skin, and said outer ply being stiffer than said inner ply for sufficient rigidity of said strap against self-folding upon itself, with said outer ply being of cured rubber to serve as a non-skid backing for the wound-on tapes to hold them against creepage on said strap.

2. An ankle tape pack, comprising a strap having inner and outer plies and being shaped for wear on an ankle and adjoining instep of a foot, and tapes attached with one end to said strap and adapted for winding on said strap when worn on an ankle and adjoining instep of a foot to thereby hold the ankle taped, with said inner ply being of sock material for direct wear on a wearer's skin, and said outer ply being stiffer than said inner ply for sufficient rigidity of said strap against self-folding upon itself, with said outer ply being of a material of a coefficient of sliding friction substantially like that of cured rubber, whereby said outer ply serves as a non-skid backing for the wound-on tapes to hold them against creepage on said strap, said strap has an instep portion with opposite side edges, and an ankle portion of which a first length is continuous with said instep portion and has opposite side edges continuous with those of said instep portion, and an endlength continuous with said first length and being in the form of a sleeve for slip onto an ankle, with said instep portion and first length of said ankle portion being shaped and sized for wrapping onto the instep and ankle of feet of different sizes in substantial form-fit therewith.

3. An ankle tape pack, comprising a strap having inner and outer plies and being shaped for wear on an ankle and adjoining instep of a foot, and tapes attached with one end to said strap and adapted for winding on said strap when worn on an ankle and adjoining instep of a foot to thereby hold the ankle taped, with said inner ply being of a sock material, and said outer ply being of a woven stretch fabric next to said inner ply and having an outer coating of a material of a coefficient of sliding friction substantially like that of cured rubber, whereby said outer ply serves as a non-skid backing for the wound-on tapes to hold them against creepage on said strap, and said plies being together of a stiffness for sufficient rigidity of said strap against self-folding upon itself.

* * * * *